US007744815B2

(12) United States Patent
Bohm et al.

(10) Patent No.: US 7,744,815 B2
(45) Date of Patent: Jun. 29, 2010

(54) DEVICE FOR DETERMINING CHLORINE DIOXIDE AND METHOD

(75) Inventors: Holger Bohm, Lübeck (DE); Andreas Mohrmann, Krummesse (DE); Bettina Runge, Lübeck (DE); Armin Schulten, Lübeck (DE)

(73) Assignee: Dräger Safety AG & Co., KGaA, Lübeck (DE)

( * ) Notice: Subject to any disclaimer, the term of this patent is extended or adjusted under 35 U.S.C. 154(b) by 209 days.

(21) Appl. No.: 11/860,621

(22) Filed: Sep. 25, 2007

(65) Prior Publication Data

US 2008/0076185 A1 Mar. 27, 2008

(30) Foreign Application Priority Data

Sep. 26, 2006 (DE) ....................... 10 2006 045 406

(51) Int. Cl.
*G01N 21/78* (2006.01)

(52) U.S. Cl. ............................ 422/55; 422/59; 422/83; 422/88; 436/124

(58) Field of Classification Search ................. 436/124; 422/55, 59, 83, 88
See application file for complete search history.

(56) References Cited

U.S. PATENT DOCUMENTS

| | | | | |
|---|---|---|---|---|
| 5,283,199 | A | 2/1994 | Bacon, Jr. et al. | |
| 6,537,821 | B1 | 3/2003 | Rosenblatt et al. | |
| 6,777,242 | B1 | 8/2004 | Gautier et al. | |
| 2004/0161367 | A1 * | 8/2004 | Truex et al. | 422/59 |
| 2004/0166553 | A1 * | 8/2004 | Nguyen et al. | 435/15 |

FOREIGN PATENT DOCUMENTS

| | | |
|---|---|---|
| DE | 1 250 658 | 4/1968 |
| DE | 199 60 275 A1 | 6/2001 |
| DE | 102 25 626 A1 | 12/2003 |
| EP | 0 054 957 | 6/1982 |
| JP | 61 18041 | 4/1994 |

* cited by examiner

*Primary Examiner*—Robert J Hill, Jr.
*Assistant Examiner*—Dwan A Gerido
(74) *Attorney, Agent, or Firm*—McGlew and Tuttle, P.C.

(57) ABSTRACT

A device and a method are provided for determining chlorine dioxide, especially in the presence of chlorine as a foreign gas. In the device the gas sample is exposed at first to a reagent for removing chlorine and subsequently to an indicator or to an electrochemical cell for the qualitative and/or quantitative determination of chlorine dioxide. The reagent for removing chlorine is or contains cyclohexylsulfamic acid and/or salts thereof. The device, through which flow can take place may be a test tube.

20 Claims, 3 Drawing Sheets

DEVICE FOR DETERMINING CHLORINE DIOXIDE AND METHOD

CROSS REFERENCE TO RELATED APPLICATIONS

This application claims the benefit of priority under 35 U.S.C. §119 of German Patent Application DE 10 2006 045 406.5 filed Sep. 26, 2006, the entire contents of which are incorporated herein by reference.

FIELD OF THE INVENTION

The present invention pertains to a device and a method for determining chlorine dioxide especially in the presence of chlorine as a foreign gas.

BACKGROUND OF THE INVENTION

Corresponding to its oxidation states, chlorine forms a number of oxides, which readily decompose, in general, in the presence of oxidizable substances, at times even accompanied by explosion. Oxides of chloride, e.g., dichlorine monoxide ($Cl_2O$), dichlorine trioxide ($Cl_2O_3$), dichlorine hexoxide ($Cl_2O_6$), dichlorine heptoxide ($Cl_2O_7$), and chlorine dioxide ($ClO_2$) are known.

Chlorine dioxide is the only chlorine oxide to have acquired industrial significance. It is prepared, e.g., from sodium chlorate in an acid environment in the presence of chloride ($ClO_3^-+Cl^-+2H+\rightarrow ClO_2+½Cl2+H_2O$). Chlorine dioxide can also be prepared from aqueous solutions containing sodium chlorite by oxidation with chlorine ($2ClO_2^-+Cl_2\rightarrow 2ClO_{2+2}Cl^-$) or hypochlorite ($2ClO_2^-+HOCl\rightarrow 2ClO_2+Cl^-+OH^-$). On the other hand, it is also possible to disproportionate chlorite in the presence of acid into chlorine dioxide and chloride ($5ClO_2^-+4H+\rightarrow 4ClO_2+Cl^-+2H_2O$).

Chlorine dioxide ($ClO_2$) has a molecular weight of 67.45 g/mol, is a yellowish-reddish gas, a reddish-brown liquid (boiling point 11° C.) or forms explosive red crystals (freezing point −59° C.) as a solid. The odor is similar to that of chlorine. The liquid has a density of 1.62 g/cm$^3$, and the gas has a density of 3.09 g/L. Chlorine dioxide is very readily soluble in water compared to chlorine. The MAC (maximum allowable concentration—Threshold Limit Value) is 0.3 mg/m$^3$. Chlorine dioxide readily decomposes into chlorine ($Cl_2$) and oxygen and therefore often exists together with oxygen and chlorine in the gaseous state.

Chlorine dioxide is a chlorine compound that is used for bleaching in the textile, pulp and paper industry, e.g., for bleaching oils, fats and waxes. Furthermore, it is a disinfectant, which is also used in food processing plants. Chlorine dioxide is also used as a water disinfectant, as well as for disinfecting and deodorizing foul-smelling wastes and wastewaters.

In many cases, chlorine dioxide has industrial and/or ecological advantages over chlorine and forms, as a rule, a markedly smaller quantity of byproducts than chlorine, which can be used mostly as an alternative. Thus, chlorine dioxide is a proven agent for disinfecting pool water, shower water and drinking water.

It is necessary to monitor minimum and maximum concentrations at the site of use when chlorine dioxide disinfection is used. Chemical methods by means of redox indicators and the color change thereof are available for this. Automated determinations of the chlorine dioxide concentrations use electrochemical methods such as amperometric measurements or determinations of the redox potential. It is also possible to determine chlorine dioxide by means of gas sensors, e.g., on the basis of the redox potential. These methods detect cumulative parameters and are not usually specific for chlorine dioxide, but also detect other oxidizing substances.

Since chlorine dioxide decomposes into chlorine and oxygen, chlorine dioxide and chlorine frequently occur in the presence of each other. Both substances are oxidants and they are therefore indicated together quasi as a cumulative value by usual chlorine test tubes that operate with a redox indicator, but it is not possible to determine whether the individual substances present in the test gas have contributed to the test results and if so, to what extent. However, it is desirable for many applications to detect chlorine dioxide selectively even in the presence of chlorine and possibly even of oxygen.

The effect of other oxidizing agents on the chlorine dioxide determination in gas samples is known per se. For example, according to JP 61-18041, ozone and hypochloride present in the carrier gas are decomposed and bound on manganese dioxide and strongly basic ion exchange resin, so that chlorine dioxide can be determined free from these foreign gases by means of a semiconductor sensor. According to US 2004/0161367, sulfamic acid is used to trap chlorine in a test tube.

SUMMARY OF THE INVENTION

The object of the present invention is to provide a device and a method for the simple determination of chlorine dioxide, especially of chlorine dioxide in the presence of oxygen and chlorine, into which chlorine dioxide readily decomposes. The object is accomplished according to the present invention by the subject of the independent claims. Preferred embodiments are the subject of the subclaims or will be described below.

It was surprisingly found that when a test gas containing chlorine and chlorine dioxide is passed over cyclohexylsulfamic acid (CAS No.: 100-88-9)

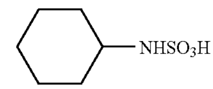

and/or salts thereof (hereinafter called reagent for short), gaseous chlorine is selectively bound, but chlorine dioxide passes through the reagent. The reagent is preferably the only chlorine trap used.

Furthermore, the present invention pertains to a test tube, which has a prelayer, through which the chlorine dioxide can pass essentially unhindered but which binds or adsorbs chlorine, in front of the indicator layer proper having the indicator, relative to the passage of the test gas.

According to the invention, a device is provided through which a gas sample can flow, for detecting chlorine dioxide, optionally in the presence of chlorine. In the device the gas sample to be analyzed is exposed at first to a reagent for removing chlorine and subsequently to an indicator or to an electrochemical cell for the qualitative and/or quantitative determination of chlorine dioxide, wherein the reagent for removing chlorine is or contains cyclohexylsulfamic acid and/or salts thereof.

The reagent for removing chlorine may be sodium N-cyclohexyl sulfamate and/or calcium N-cyclohexyl sulfamate.

The indicator may be a colorimetric indicator, preferably a benzidine derivative.

The chlorine dioxide indicator may be N,N-diethyl-p-phenylenediamine, alizarine violet 3R, 3,3',5,5'-tetramethylbenzene-diphenylbenzidine, chlorophenol red, methylene blue, N,N,N',N'-tetraphenylbenzidine, o-tolidine and/or o-dianisidine, especially 3,3',5,5'-tetramethylbenzene-diphenylbenzidine, o-tolidine and/or o-dianisidine.

The device, through which flow can take place, may advantageously be a test tube, and the reagent and the indicator may be stored in same separated from each other, optionally by quartz glass powder, in at least two separate containers or areas, which are connected for the flowing gas. The two containers or areas may be part of a transparent test tube. The two containers may form part of two tubes, which together form the test tube.

According to a further aspect of the invention, a method for detecting chlorine dioxide is provided in which the gas sample to be analyzed is exposed at first to a reagent for removing chlorine and subsequently to an indicator or to an electrochemical cell for the qualitative or quantitative determination of chlorine dioxide. The reagent for removing chlorine is or contains cyclohexylsulfamic acid and/or salts thereof.

A defined quantity of sample gas may be drawn through a test tube, optionally a multi-part test tube, by means of a hand pump, in order to be contacted with the reagent for removing chlorine, and with the indicator, especially for the quantitative determination of chlorine dioxide.

The various features of novelty which characterize the invention are pointed out with particularity in the claims annexed to and forming a part of this disclosure. For a better understanding of the invention, its operating advantages and specific objects attained by its uses, reference is made to the accompanying drawings and descriptive matter in which preferred embodiments of the invention are illustrated.

DESCRIPTION OF THE PREFERRED EMBODIMENTS

Figure 1:
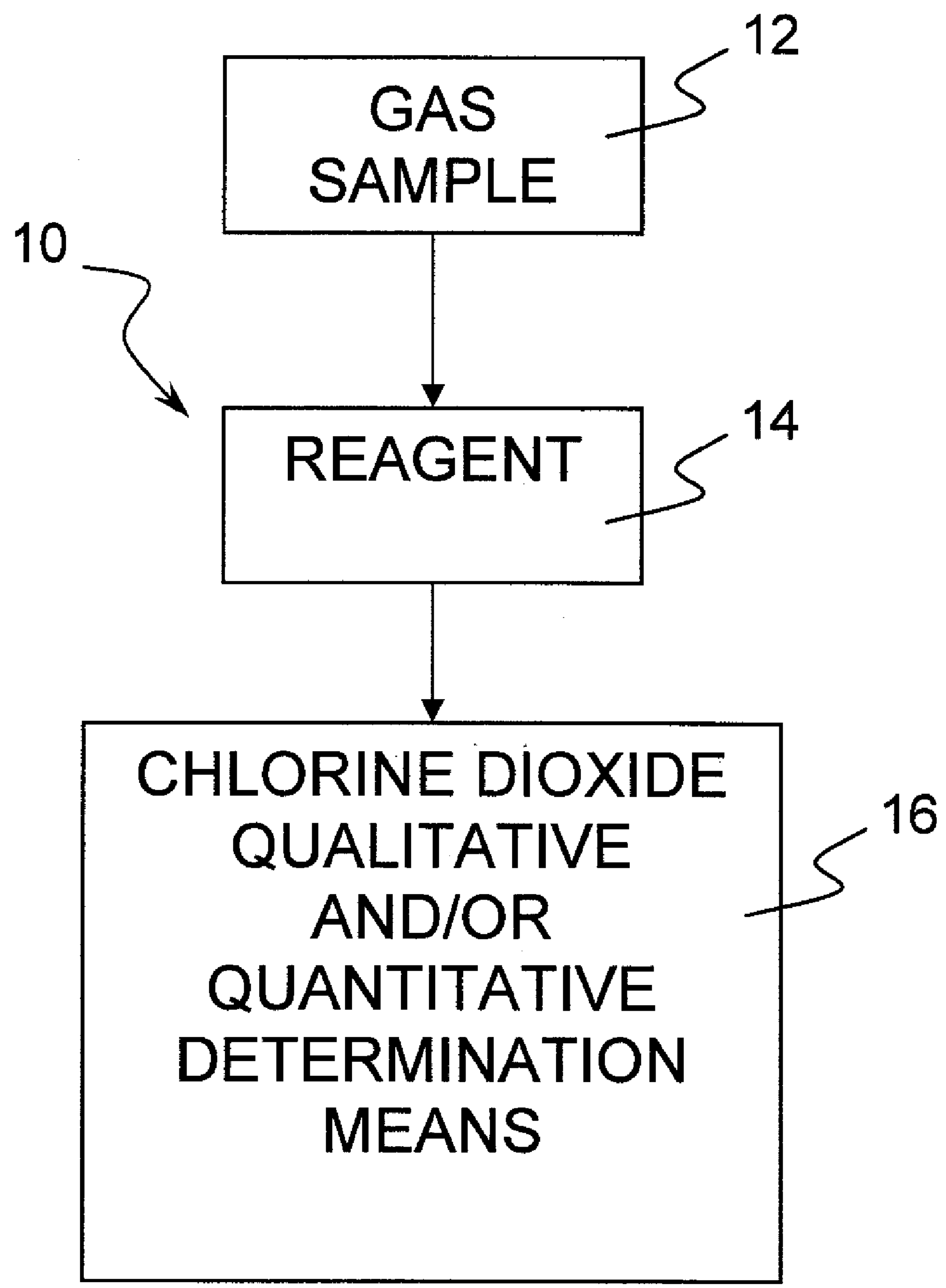
FIG. 1 is a schematic view showing features of the device according to the invention.

Referring to the drawings in particular, FIG. 1 shows in a schematic view the features of a device 10 through which a gas sample can flow, for detecting chlorine dioxide, optionally in the presence of chlorine. In the device the gas sample 12 to be analyzed is exposed at first to a reagent flow space with reagent 14 for removing chlorine. The reagent 14 for removing chlorine is or contains cyclohexylsulfamic acid and/or salts thereof. Cyclohexylsulfamic acid salts are known as, e.g., sodium N-cyclohexyl sulfamate or calcium N-cyclohexyl sulfamate (CAS 139-06-0), also called sodium cyclamate and calcium cyclamate, respectively, and are used as synthetically prepared sweeteners under the name cyclamate (E 952). The gas sample to be analyzed is subsequently exposed to chlorine dioxide qualitative and/or quantitative determination means 16 for the qualitative and/or quantitative determination of chlorine dioxide. The chlorine dioxide determination means 16 may be an indicator 18 or an electrochemical cell. The indicator may be a calorimetric indicator, preferably a benzidine derivative. The following shall be mentioned as examples of indicators for the determination of chlorine dioxide according to the present invention: N,N-diethyl-p-phenylenediamine (DPD), Alizarine Violet 3R (CAS 6408-63-5), 3,3,5,5-tetramethylbenzene-diphenylbenzidine, chlorophenol red, methylene blue, N,N,N',N'-tetraphenylbenzidine, o-tolidine (3,3'-dimethylbenzidine) and/or o-dianisidine (3,3'-dimethoxybenzidine). Benzidine derivatives, such as 3,3,5,5-tetramethylbenzene-diphenylbenzidine, N,N,N',N'-tetraphenylbenzidine, o-tolidine and/or o-dianisidine are preferred. The indicators are redox indicators and can be used as colorimetric indicators.

The chlorophenol red method is based on the ability of chlorine dioxide to selectively (quantitatively) reduce the color of chlorophenol red. According to the DPD-glycine test, chlorine is bound by glycine (foreseeably as chloroaminoacetic acid) and chlorine dioxide forms a pink color with DPD, and the intensity of this color is proportional to the chlorine dioxide concentration. Chlorine dioxide exerts a decoloring effect on the indicator Alizarine Violet 3R in the alkaline range (e.g., by means of the buffer $NH_3$—$NH_4Cl$ at pH 8.1 to 8.5).

The indicator and/or the reagent can be applied to a granular material such as silica gel.

Atmospheric chlorine dioxide can thus also be determined quantitatively by taking up a gas volume, preferably a defined gas volume, and passing it through the test tube/test tubes.

Figure 2:
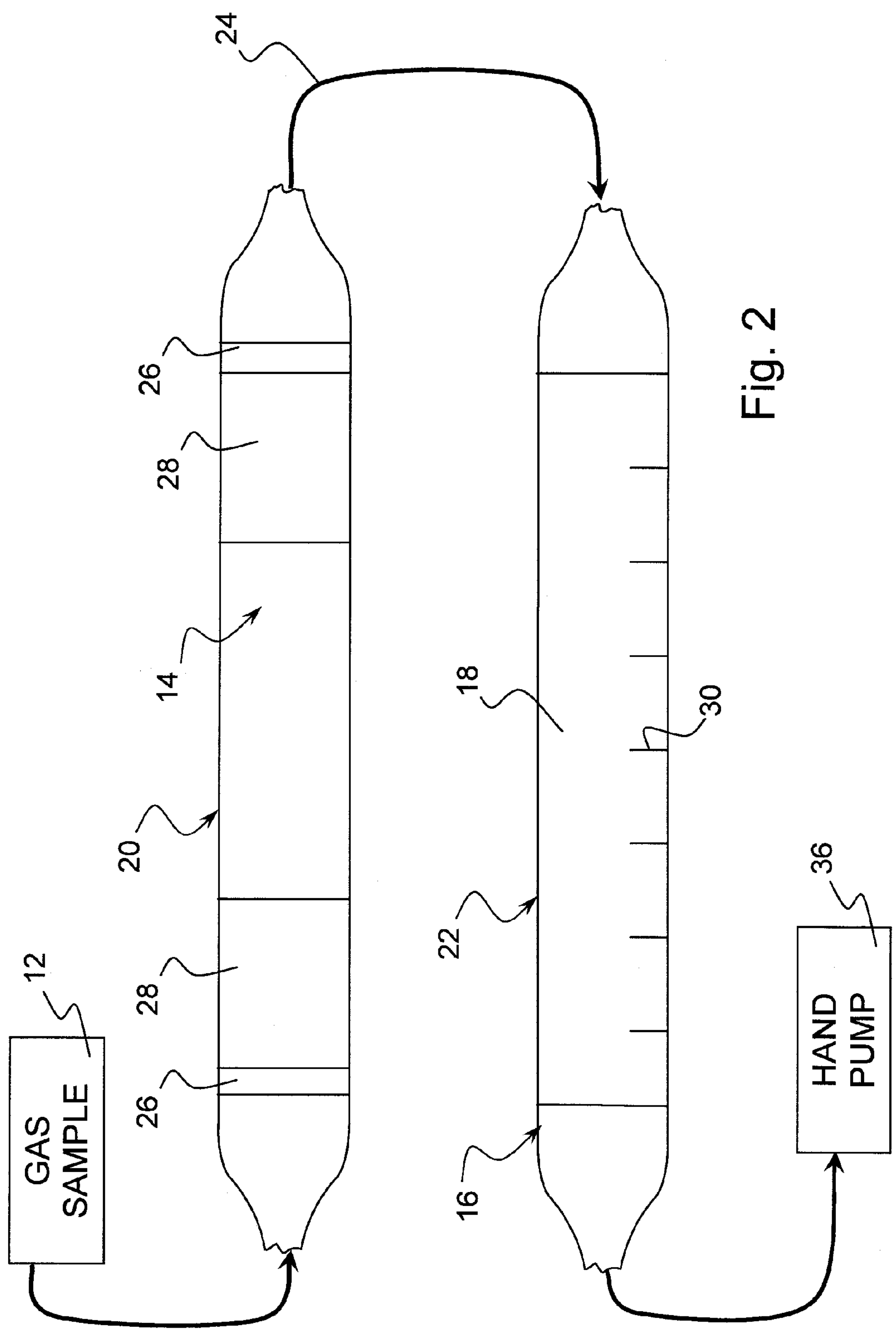
FIG. 2 is a simplified diagram depicting a detection tube according to one embodiment of the invention.
Figure 3:
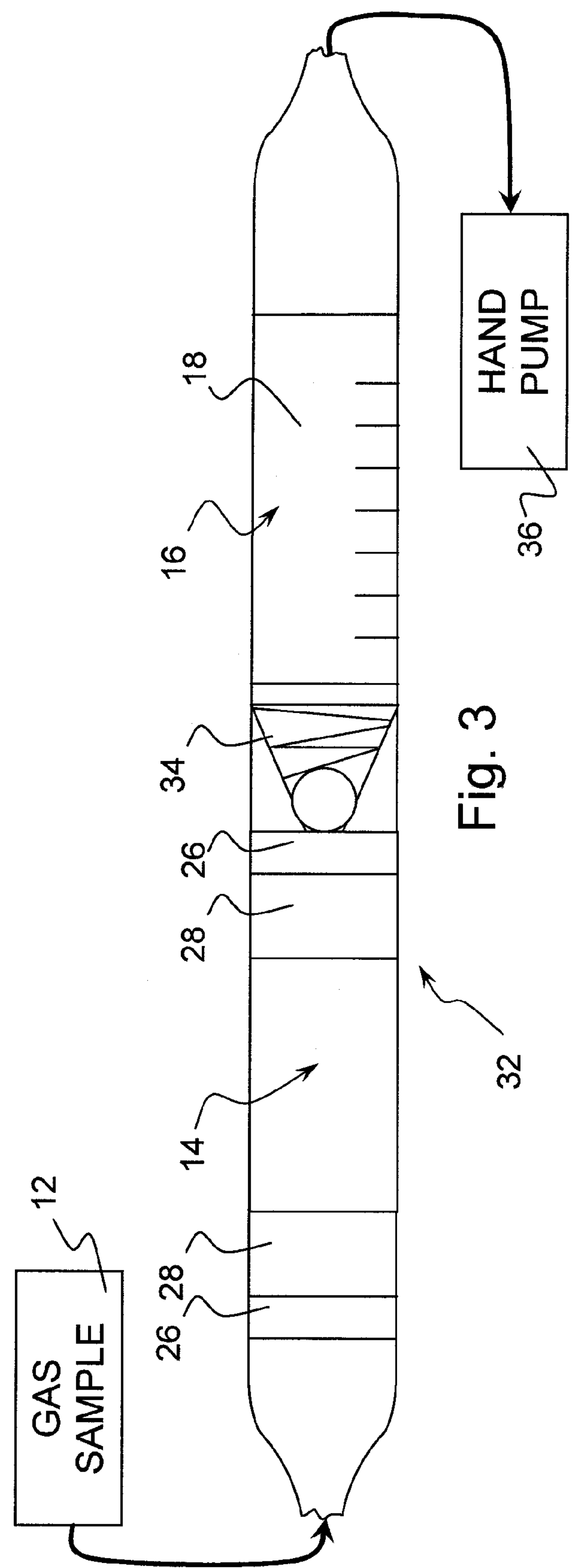
FIG. 3 is a simplified diagram depicting a detection tube according to another embodiment of the invention.

FIG. 2 shows an embodiment of the present invention in which an upstream test tube generally designated 20, is followed downstream by a calorimetric test tube generally designated 22 forming the chlorine dioxide determination means 16 for chlorine dioxide. The test tubes 20 and 22 are connected to one another, e.g., by a tube 24. The upstream tube contains the reagent 14, e.g., between at least two holding elements 26, e.g., in the form of a sintered glass bottom, and, if desired, also between two quartz glass powder or glass wool layers 28. The quartz glass powder or glass wool layers 28 can be used to prevent the adsorbent from trickling through the holding elements 26. At the same time, the adsorbent can be mixed with quartz glass powder in order to guarantee better contacting of the gas with the reagent.

The colorimetric test tube 22 contains an indicator layer consisting essentially of one of the above-mentioned indicators 18, optionally additionally with a color scale and/or with a measuring range 30, preferably from 0.025 ppm to 1 ppm, depending on the progression of the color trace along the indicator for determining the chlorine dioxide concentration. A defined quantity of sample gas is drawn through the test tubes 20 and 22, by means of a hand pump 36, in order to be contacted with the reagent 14 for removing chlorine, and with the indicator 18, for the quantitative determination of chlorine dioxide.

According to another embodiment of the present invention, the essentially one-part test tube 32 has a separated prelayer containing the reagent trap 14, through which the quantity of sample gas flows, the sample gas leaving the prelayer in the form of a gas that has been freed from chlorine, in order to flow to the indicator layer forming chlorine dioxide determination means 16 containing the indicator 18 for chlorine dioxide. If desired, the prelayer with reagent 14 and the indicator layer forming chlorine dioxide determination means 16 may be provided with a valve element 34 opening during the flow only. In an advantageous embodiment of the present invention, the valve element 34 may consist of a spring-loaded plate valve or ball valve. This will then act as a non-return valve in a simple manner.

The test tube 32 preferably has two tips (shown broken away), which can be broken off, and the prelayer and the indicator layer in the direction of flow. The two layers are separated from each other by an intermediate layer, which consists of one or more gas-permeable holding elements 26, and optionally with a valve 34 formed between them. With the test tube opened on both sides, e.g., by means of broken-off tips, a defined quantity of gas flows through the test tube, e.g., through a hand pump attached to one end. A defined quantity of sample gas is drawn through the test tube 32, by means of the hand pump 36, in order to be contacted with the reagent 14 for removing chlorine, and with the indicator 18, for the quantitative determination of chlorine dioxide.

While specific embodiments of the invention have been shown and described in detail to illustrate the application of the principles of the invention, it will be understood that the invention may be embodied otherwise without departing from such principles.

What is claimed is:

1. A device, through which a gas sample can flow, for detecting chlorine dioxide, the device comprising:

a reagent flow space;

a reagent in said flow space, said flow space to expose the gas sample to be analyzed to said reagent for removing chlorine, said reagent containing one or more of cyclohexylsulfamic acid and a cyclohexylsulfamic acid salt; and an indicator or an electrochemical cell forming a chlorine dioxide qualitative and/or quantitative determination means for a qualitative and/or quantitative determination of chlorine dioxide.

2. A device in accordance with claim 1, wherein the reagent for removing chlorine is sodium N-cyclohexyl sulfamate and/or calcium N-cyclohexyl sulfamate.

3. A device in accordance with claim 1, the indicator for chlorine dioxide is N,N-diethyl-p-phenylenediamine, alizarine violet 3R, 3,3',5,5'-tetramethylbenzene-diphenylbenzidine, chiorophenol red, methylene blue, N,N,N',N'-tetraphenylbenzidine, o-tolidine, o-dianisidine, 3,3',5,5'-tetramethylbenzene-diphenylbenzidine, o-tolidine and/or o-dianisidine.

4. A device in accordance with claim 1, wherein:

said reagent flow space comprises a test tube with said reagent therein; and said chlorine dioxide determination means comprises a test tube.

5. A device in accordance with claim 1, wherein the indicator is a colorimetric indicator.

6. A device in accordance with claim 5, wherein said colorimetric indicator is a benzidine derivative.

7. A device in accordance with claim 1, wherein said reagent flow space and said chlorine dioxide determination means together comprise a test tube, and said reagent and said indicator are stored in said test tube separated from each other by a separator.

8. A device in accordance with claim 7, wherein said separator includes quartz glass powder, in at least two separate containers or areas, which are connected for a flowing gas.

9. A device in accordance with claim 8, wherein the two containers or areas are part of said test tube and said test tube is transparent.

10. A method for detecting chlorine dioxide in a gas sample, the method comprising:

exposing the gas sample to be analyzed to a reagent for removing chlorine; and subsequent to said step of exposing the gas sample to the reagent, passing the gas sample to a chlorine dioxide determination means comprising an indicator or an electrochemical cell for the qualitative or quantitative determination of chlorine dioxide, wherein the reagent for removing chlorine is or contains one or more of cyclohexylsulfamic acid and a cyclohexylsulfamic acid salt.

11. A method in accordance with claim 10, wherein the reagent for removing chlorine is sodium N-cyclohexyl sulfamate and/or calcium N-cyclohexyl sulfamate.

12. A method in accordance with claim 10, wherein the indicator is N,N-diethyl-p-phenylenediamine, alizanne violet, 3,3',5,5'-tetramethylbenzene-diphenylbenzidine, chlorophenol red, methylene blue, N,N,N',N'-tetraphenylbenzidine, o-tolidine and/or o-dianisidine, 3,3',5',5'-tetramethylbenzene-diphenylbenzidine, o-tolidine and/or o-dianisidine.

13. A method in accordance with claim 10, wherein a defined quantity of sample gas is drawn through a reagent space containing the reagent and through the chlorine dioxide determination means by means of a hand pump, in order for the sample gas to be contacted with the reagent for removing chlorine, and for the quantitative determination of chlorine dioxide with the chlorine dioxide determination means.

14. A method in accordance with claim 10, wherein the reagent for removing chlorine consists essentially of cyclohexylsulfamic acid.

15. A method in accordance with claim 10, wherein the reagent for removing chlorine consists essentially of sodium N-cyclohexyl sulfamate.

16. A method in accordance with claim 10, wherein the reagent for removing chlorine consists essentially of calcium N-cyclohexyl sulfamate.

17. A method in accordance with claim 10, wherein the indicator is a colorimetric indicator.

18. A method in accordance with claim 17, wherein said colorimetric indicator is a benzidine derivative.

19. A device, through which a gas sample can flow, for detecting chlorine dioxide, the device comprising:

a reagent flow space;

a reagent in said flow space, said flow space to expose the gas sample to be analyzed to said reagent for removing chlorine, said reagent consisting essentially of one or more of cyclohexylsulfamic acid, and a cyclohexylsulfamic acid salt; and an indicator or an electrochemical cell forming a chlorine dioxide qualitative and/or quantitative determination means for a qualitative and/or quantitative determination of chlorine dioxide downstream of said flow space.

20. A device in accordance with claim 19, wherein the reagent for removing chlorine is sodium N-cyclohexyl sulfamate and/or calcium N-cyclohexyl sulfamate.

* * * * *